United States Patent

Ogata et al.

Patent Number: 5,606,080
Date of Patent: Feb. 25, 1997

[54] TOCOPHEROL DERIVATIVES

[75] Inventors: Kazumi Ogata, Toyonaka; Hidetoshi Nakao, Amagasaki, both of Japan

[73] Assignee: Senju Pharmaceutical Co., Ltd., Osaka, Japan

[21] Appl. No.: 438,971

[22] Filed: May 11, 1995

[30] Foreign Application Priority Data

May 20, 1994 [JP] Japan ................................ 6-106484

[51] Int. Cl.$^6$ .................... C07D 311/72; C07D 405/10
[52] U.S. Cl. ............................ 549/408; 548/525
[58] Field of Search ............................ 549/408; 548/525

[56] References Cited

FOREIGN PATENT DOCUMENTS 2014879  4/1970  France .

OTHER PUBLICATIONS

Fujimoto Pharmaceutical, Chemical Abstracts, vol. 98, No. 15, 11 Apr. 1983 Abstract No. 125878x JP-A-57 175 186.

*Primary Examiner*—Nicky Chan
*Attorney, Agent, or Firm*—Wenderoth, Lind & Ponack

[57] ABSTRACT

Tocopherol derivatives of the following formula (I) or a pharmacologically acceptable salt thereof

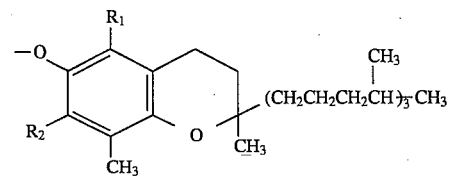

wherein $R_1$ and $R_2$ are the same or different and each represents hydrogen or methyl; $R_3$ represents an α-amino acid, ω-amino acid, or peptide bonding via the N terminus thereof, except that in the case of cysteine or glutathione which has a thiol group, bonding via the thiol group, are water-soluble and can be expected to be of use as a cerebral function-improving drug and an anticataract drug. Moreover, these compounds are of value as an UV-absorber, a skin care ingredient, or a stabilizer for other cosmetic ingredients.

7 Claims, 3 Drawing Sheets

TOCOPHEROL DERIVATIVES

BACKGROUND OF THE INVENTION

1. Field of the Invention

This invention relates to a novel and useful tocopherol derivative and a process for producing said derivative.

2. Description of the Prior Art

For the therapy of hypertension and extrasystolic abnormalities, 2,5,7,8-tetramethyl-2-(4'8'12'-trimethyltridecyl)-6-(2"-hydroxy-8"-isopropylaminopropoxy)chroman (JP Kokai Publication S-57-175186) is already known.

Under the circumstances, the inventors of this invention explored for new and useful chroman compounds in earnest and succeeded in synthesizing the compound of this invention.

This invention provides a novel and useful tocopherol derivative and a process for producing the derivative.

SUMMARY OF THE INVENTION

This invention, therefore, is directed to:

A tocopherol derivative of the following formula (I) or a pharmacologically acceptable salt thereof

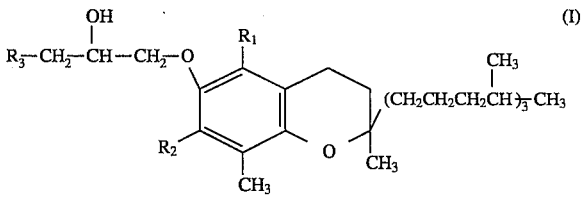

wherein $R_1$ and $R_2$ are the same or different and each represents hydrogen or methyl; $R_3$ represents an α-amino acid, ω-amino acid, or peptide bonding via the N terminus thereof, except that in the-case of cysteine or glutathione which has a thiol group, bonding via the thiol group.

(2) The tocopherol derivative or pharmacologically acceptable salt thereof as defined under (1) wherein $R_3$ is cysteine.

(3) The tocopherol derivative or pharmacologically acceptable salt thereof as defined under (1) wherein $R_3$ is taurine.

(4) The tocopherol derivative or pharmacologically acceptable salt thereof as defined under (1) wherein $R_3$ is 7-aminobutyric acid.

(5) The tocopherol derivative or pharmacologically acceptable salt thereof as defined under (1) wherein $R_3$ is glutathione.

(6) The tocopherol derivative or pharmacologically acceptable salt thereof as defined under (1) wherein $R_3$ is aspartic acid.

(7) The tocopherol derivative or pharmacologically acceptable salt thereof as defined under (1) wherein $R_3$ is glutamic acid.

(8) A process for producing a tocopherol derivative of the following formula (I) or a pharmacologically acceptable salt thereof,

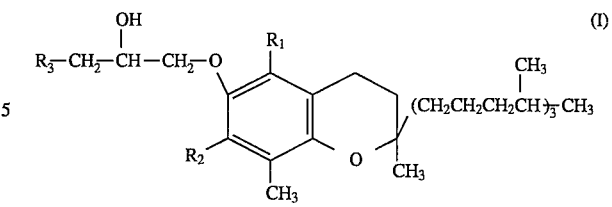

wherein $R_1$ and $R_2$ are the same or different and each represents hydrogen or methyl; $R_3$ represents an α-amino acid, ω-amino acid, or peptide bonding via the N terminus thereof, except that in the case of cysteine or glutathione which has a thiol group, bonding via the thiol group, which comprises reacting a compound of the following formula (II)

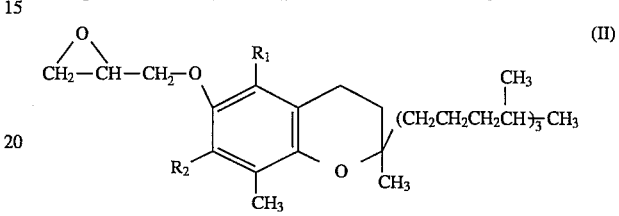

wherein $R_1$ and $R_2$ are the same or different and each represents hydrogen or methyl, with an α-amino acid, ω-amino acid or peptide in the presence of alkali.

DETAILED DESCRIPTION OF THE INVENTION

Figure 1:
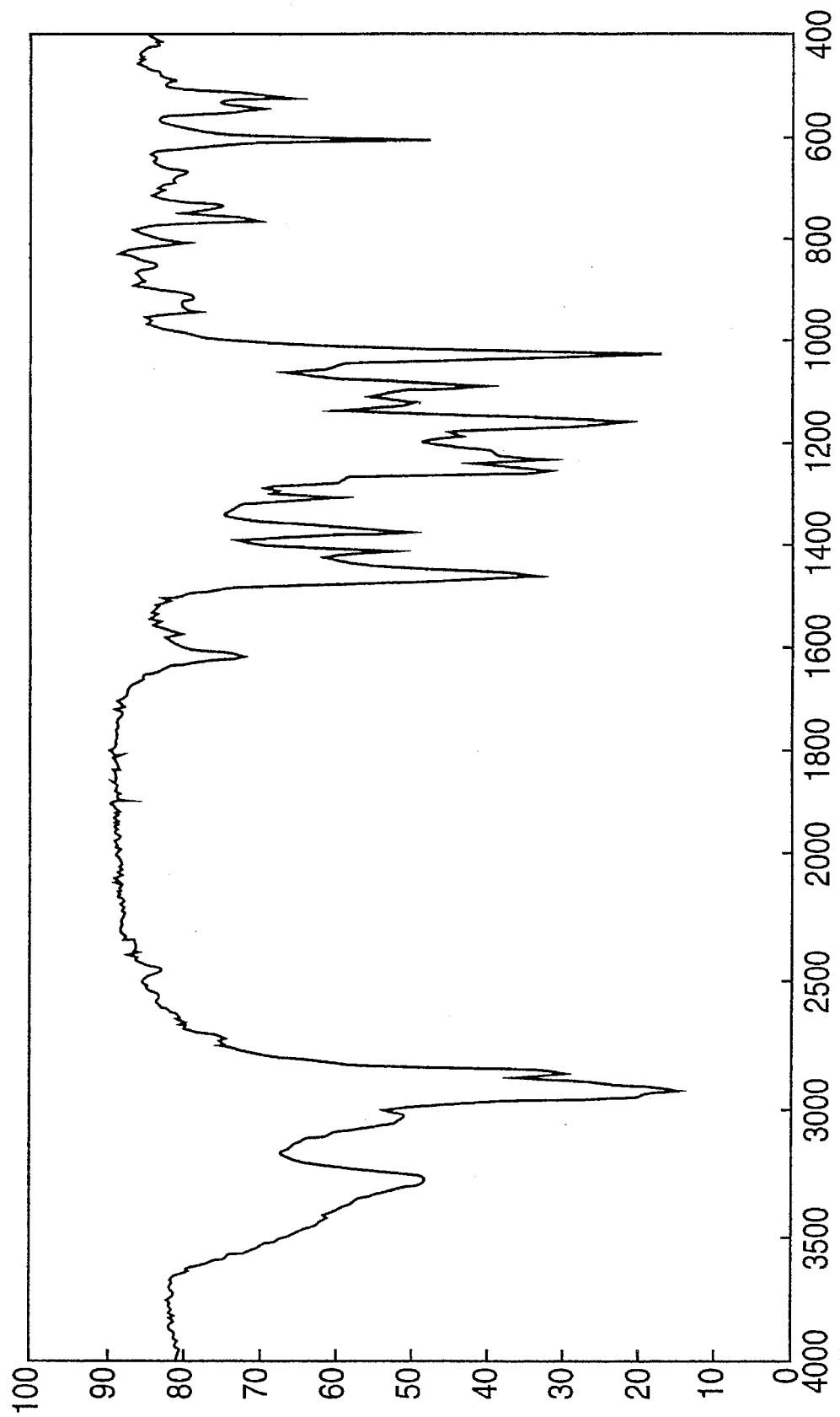
FIG. 1 is an infrared absorption spectrum (IR) of the compound synthesized in Example 1.

Referring to the above formula (I), the amino acid $R_3$ includes α-amino acids and ω-amino acids and the peptide $R_3$ includes peptides containing a cysteine structure. Among said α-amino acids are glycine, alanine, proline, cysteine, glutamic acid and so on. Among said ω-amino acids are β-alanine, γ-aminobutyric acid, ε-aminocaproic acid, etc., and as a special amino acid, 2-aminoethanesulfonic acid (taurine) can also be mentioned. The peptide $R_3$ may for example be glutathione.

The present compound of formula (I) can be synthesized in good yield by reacting a compound of formula (II) with any of the amino acids and peptides typically mentioned above in the presence of alkali under heating. The process of this invention for the production of the present compound is now described in detail.

The compound of formula (II) can be produced by, inter alia, the process described in JP Kokai Application H-5-331166, namely by heating α, β, γ or δ-tocopherol and epichlorohydrin in the presence of alkali at the reflux temperature. The α, β, γ or δ-tocopherol to be submitted to this reaction may be whichever of the DL-compound and the D-compound. The alkali for use in this reaction includes alkali hydroxides (e.g. sodium hydroxide, potassium hydroxide, etc.) and organic amines (e.g. pyridine, triethylamine, etc.), among others. This reaction process goes to completion in about 1 to 5 hours under reflux conditions.

The resulting compound of formula (II) is then reacted with said α-amino acid, ω-amino or peptide in the presence of said alkali under heating, whereby the corresponding compound of formula (I) is obtained in good yield. While this reaction proceeds in the absence of a solvent, the use of a solvent is preferred. Any reaction solvent can be employed only if it does not interfere with the reaction. Generally, a mixture of an alcohol (e.g. methanol, ethanol, etc.) with dioxane, an ether, a ketone (e.g. acetone, methyl ethyl ketone, etc.), tetrahydrofuran (THF) or the like is preferred. The alkali that can be used for this reaction includes alkali hydroxides (e.g. sodium hydroxide, potassium hydroxide, etc.) and organic amines (e.g. pyridine, triethylamine, etc.), among others. This reaction process goes to completion in about 1 to 5 hours under reflux conditions. Finally, the present compound is isolated and purified by recrystallization from a suitable solvent such as methanol and methanol-ethyl acetate.

The present compound thus obtained can be converted to a pharmacologically acceptable salt by the per se known procedure. This conversion to the salt can be carried out after isolation of the free compound from the reaction mixture or prior to the isolation.

The compound obtained in the above manner can be used for purposes of this invention, regardless of whether it is the free compound or a pharmacologically acceptable salt. The salt includes salts with alkali metals such as sodium, potassium, etc., salts with alkaline earth metals such as calcium, magnesium, etc., salts with inorganic acids such as hydrochloric acid, sulfuric acid, etc., and salts with organic acids such as acetic acid and so on. Any other salt can also be used only if it is pharmacologically acceptable.

The present compound thus obtained is a novel tocopherol derivative not described in the literature before and can be expected to find application as a cerebral function improving agent or an anticataract agent. Moreover, because the present compound has humectant activity, it is of value as a cosmetic ingredient.

Generally speaking, few tocopherol derivatives are water-soluble but alkali salts of the present compound of formula (I) wherein $R_3$ is glutamic acid, aspartic acid or glutathione have the advantage of being highly water-soluble.

For use of the present compound as a cosmetic ingredient, it can be incorporated in cream, lotion and toilet water formulations as a humectant intended for absorption of ultraviolet radiation and protection of the skin or stabilizing other cosmetic ingredients.

For the prevention and treatment of the diseases mentioned hereinbefore, the present compound can be administered orally or otherwise. The pharmaceutical dosage form that can be employed includes solid dosage forms such as tablets, granules, powders, capsules, ointments, suppositories, etc. and liquid dosage forms such as eye-drops, injections, syrups, etc. and these dosage forms can be respectively manufactured by the routine pharmaceutical procedures. These preparations may be supplemented with a variety of conventional additives such as excipients, binders, disintegrators, thickeners, dispersants, reabsorption promoters, buffers, surfactants, preservatives, isotonizing agents, stabilizers and pH control agents.

When the present compound is incorporated in cosmetic preparations, too, a variety of ingredients used generally in cosmetic formulations can be added in suitable amounts.

For use of the present compound as a drug or a cosmetic ingredient, one or more species of the compound can be used according to the intended application and need.

The dosage of the present compound as a drug is dependent on the species of compound, the type of disease, the patient's body weight and age, clinical symptoms to be controlled, and the route of administration, among other factors. However, taking an injection as an example, about 1 mg to about 500 mg can be administered daily to an adult. In the case of an oral preparation, about 10 mg to about 1000 mg can be administered a few times a day to an adult. For use as ophthalmic solutions, a few drops of a solution of about 0.01 (w/v) % to 0.5 (w/v) % concentration can be advantageously administered a few times daily.

For use as a cosmetic ingredient, the present compound can be added at the level of generally about 0.001 to 5 (w/w) %, preferably about 0.01 to 2 (w/w) %, although the optimum amount depends on the species of compound, the kind of cosmetic product, and the objective of formulation.

EXAMPLE

The following examples and formulation examples are intended to describe this invention in further detail.

Example 1

1-(Sulfoethylamino)-3-(α-tocopher-6-yloxy)propane-2-ol

[$R_1=R_2=CH_3$, $R_3=NHCH_2CH_2SO_3H$]

In 50 ml of dioxane were dissolved 4.3 g of DL-α-tocopherol and 5 ml of epichlorohydrin followed by addition of 0.6 g of potassium hydroxide, and the mixture was refluxed for 5 hours. After the precipitated inorganic salt was filtered off, the solvent was distilled off and the oily residue was extracted with ethyl acetate. The extract was washed with water and ethyl acetate was distilled off to give 4.7 g of (2,3-epoxypropane)tocopherol as an oily residue. On the other hand, 0.4 g of sodium hydroxide was dissolved in 40 ml of methanol, and to this solution, 1.25 g of 2-aminoethanesulfonic acid was added. Then, a solution prepared by dissolving said (2,3-epoxypropane)tocopherol in 20 ml of dioxane was further added. The mixture was refluxed for 5 hours, after which the solvent was distilled off. The residue was diluted with 50 ml of water, stirred, and made acidic to hydrochloric acid. To this was added 30 ml of ethyl acetate and the mixture was allowed to stand, whereupon white crystals separated out. This crystal crop was recovered by filtration, washed with water and acetone, and recrystallized from methanol to provide 3.5 g of the title compound as white crystals. m.p. 213°–215° C. (decomp.) The infrared absorption spectrum (IR) of this compound is shown in FIG. 1.

Elemental analysis for $C_{34}H_{61}O_6NS$ Calcd. (%): C, 66.74; H, 10.05; N, 2.29 Found (%):C, 66.48; H, 9.78; N, 2.02

Example 2

1-(Carboxypropylamino)-3-(α-tocopher-6-yloxy)propane-2-ol hydrochloride

[$R_1=R_2=CH_3$, $R_3=NHCH_2C_2CH_2COOH$]

Using 4.3 g of DL-α-tocopherol and 5 ml of epichlorohydrin, (2,3-epoxypropane)tocopherol was prepared in the same manner as described in Example 1. Then, this compound was reacted with a solution prepared by dissolving 1.1 g of γ-amino-n-butyric acid and 0.4 g of sodium hydroxide in 40 ml of methanol in the same manner as Example 1 to give white crystals. The crude crystals were recrystallized from methanol-ethyl acetate to provide 3.2 g of the title compound. This crystal crop begins to melt gradually at about 125° C.

Elemental analysis for $C_{36}H_{63}O_5N \cdot HCl$ Calcd. (%): C, 69.03; H, 10.30; N, 2.24 Found (%): C, 68.96; H, 10.11; N, 2.01

Example 3

S-[3-α-Tocopher-6-yloxy)-2-hydroxypropyl]cysteine

[$R_1=R_2=CH_3$, $R_3=S-CH_2CH(NH_2)COOH$]

Figure 2:
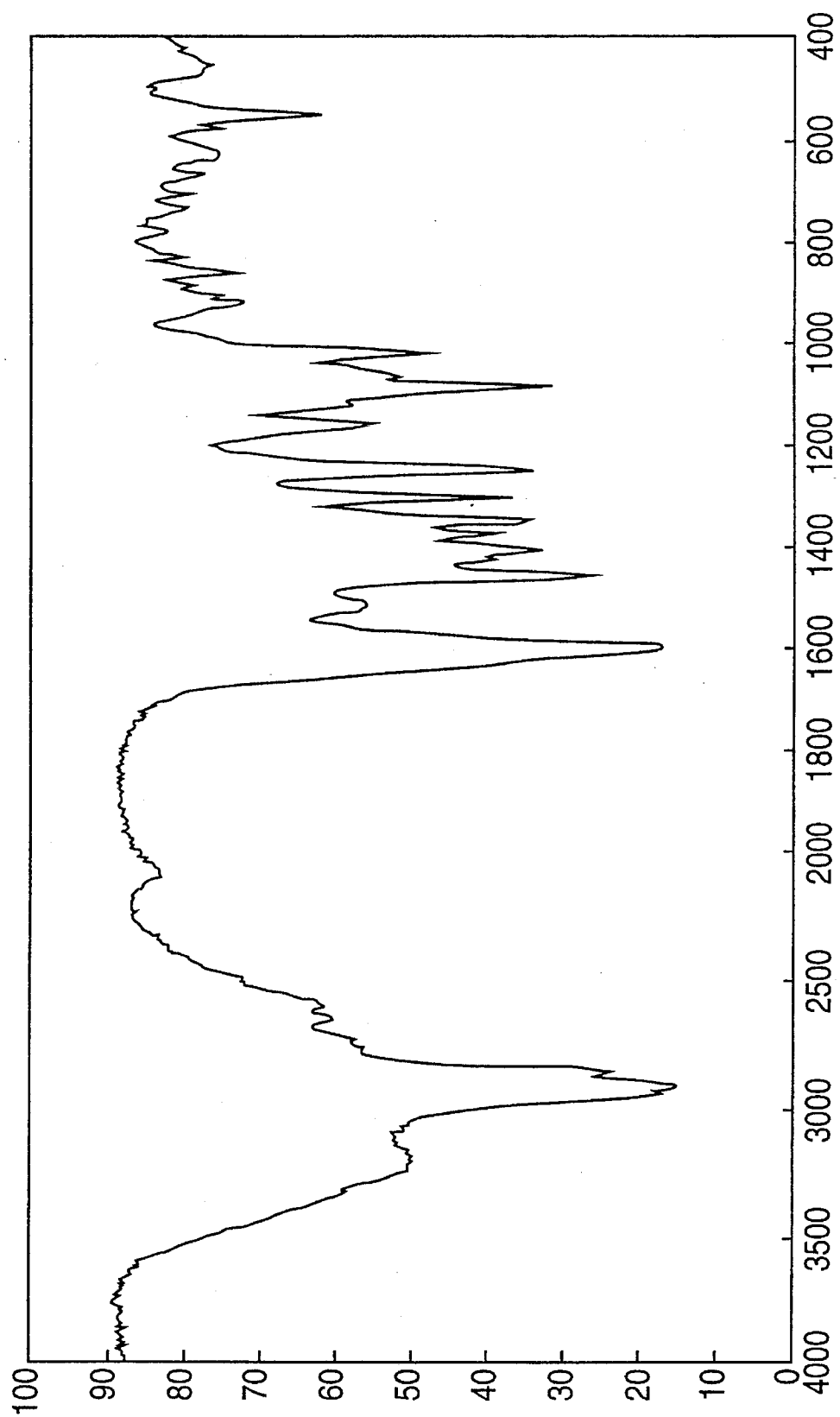
FIG. 2 is an infrared absorption spectrum (IR) of the compound synthesized in Example 3.

Using 4.3 g of DL-α-tocopherol, 5 ml of epichlorohydrin, 1.3 g of L-cysteine, and 0.44 g of sodium hydroxide, the reaction was carried out under nitrogen in otherwise the same manner as Example 1. The solvent was then distilled off and the oily residue was diluted with 150 ml of water and made acidic with acetic acid. The resulting light-yellow crystals were recovered by filtration and washed with water and acetone. The crystals were suspended in 150 ml of methanol and dissolved by alkalinizing with 2N sodium hydroxide solution. After the insoluble matter was filtered off, the filtrate was made acidic with acetic acid and the precipitated white crystals were collected by filtration. The crystals were washed with 504 methanol and dried to provide 3.8 g of the title compound. m.p. 173°–175° C. (decomp.) The infrared absorption spectrum (IR) of this compound is shown in FIG. 2.

Elemental analysis for $C_{35}H_{61}O_5NS$ Calcd. (%): C, 69.15; H, 10.11; N, 2.30 Found (%): C, 68.96; H, 10.25; N, 2.22

Example 4

S-[3-(α-Tocopher-6-yloxy)-2-hydroxypropyl]-γ-glutamylcysteinylglycine

[$R_1=R_2=CH_3$, $R_3=NH_2CH(COOH)CH_2CH_2CONHCH(CH_2S)CONHCH_2COOH$]

Figure 3:
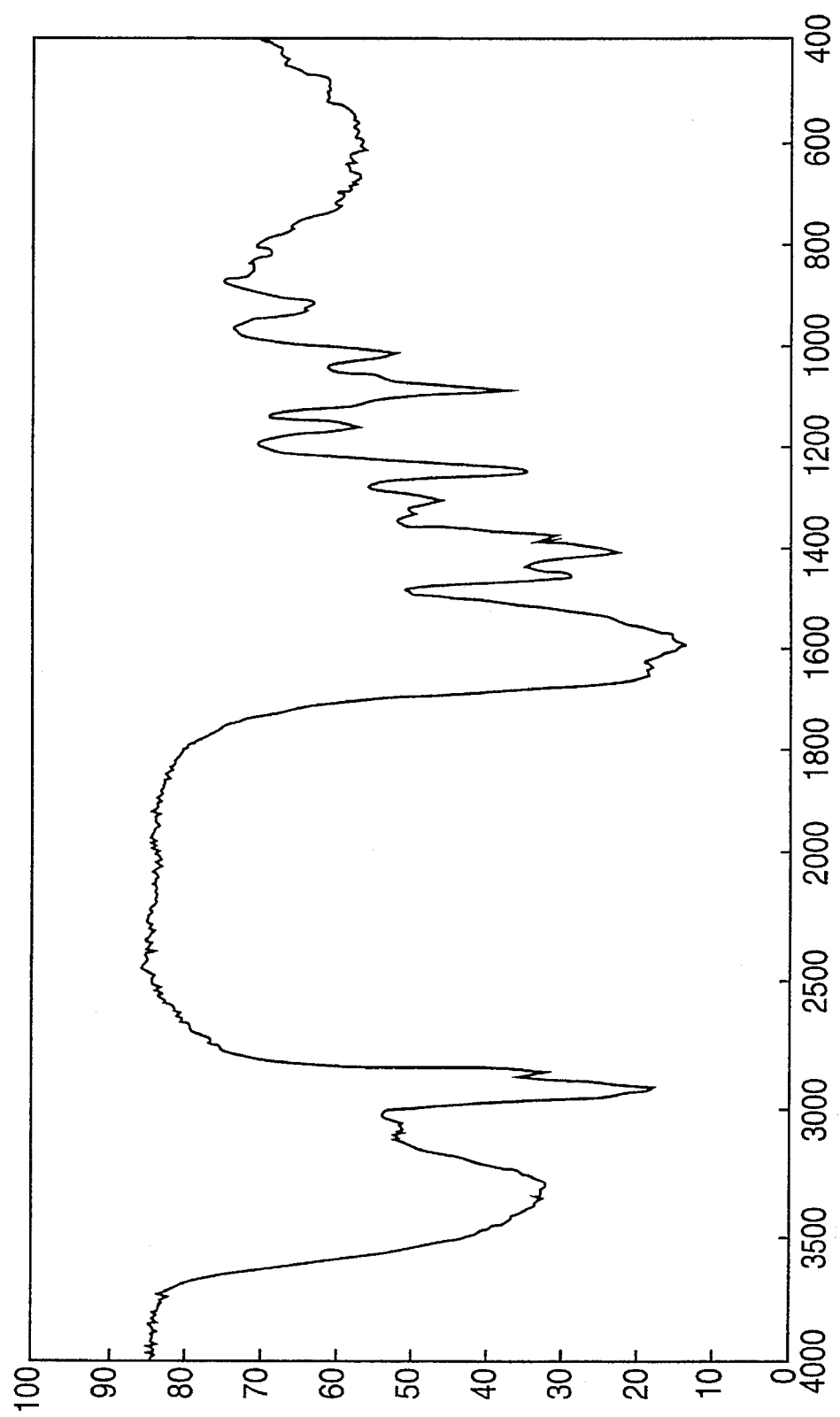
FIG. 3 is an infrared absorption spectrum (IR) of the compound synthesized in Example 4.

Using 4.3 g of DL-α-tocopherol and 5 ml of epichlorohydrin, the reaction procedure described in Example 1 was repeated to provide (2,3-epoxypropane)-tocopherol. To this compound was added 20 ml of dioxane. On the other hand, 0.8 g of sodium hydroxide was dissolved in 40 ml of methanol, and 3.2 g of glutathione and, then the above dioxane solution were added in that order. The mixture was refluxed under nitrogen for 4 hours, at the end of which time the solvent was distilled off, whereupon crystals separated out. To this system was added a further amount of dioxane for completion of crystallization and the resulting crystals crop was recovered by filtration. The crystals were dissolved in water and the solution was made acidic with acetic acid. The resulting white crystals were collected by filtration and rinsed white water. The crystals were suspended in 150 ml of methanol and dissolved by gradual addition of methanolic sodium hydroxide solution. The solution was concentrated to about 30 ml, whereupon crystals began to separate out. To this system was added ethyl alcohol and the resulting white crystals were collected by filtration to provide 4.1 g of the sodium salt of the title compound. m.p. 205°–207° C. (decomp.) The infrared absorption spectrum (IR) of this compound is shown in FIG. 3.

Elemental analysis for $C_{42}H_{69}O_9N_3SNa_2 \cdot H_2O$ Calcd. (%): C, 58.93; H, 8.36; N, 4.91 Found (%): C, 58.63; H, 8.43; N, 4.83

Example 5

N-[3-(α-Tocopher-6-yloxy)-2-hydroxypropyl] aspartic acid.

[$R_1=R_2=CH_3$, $R_3=NHCH(COOH)CH_2COOH$]

Using 4.3 g of DL-α-tocopherol and 5 ml of epichlorohydrin, the reaction procedure described in Example 1 was repeated to prepare (2,3-epoxypropane)-tocopherol. To this was added 20 ml of dioxane. Then, 1.3 g of L-ascorbic acid and 0.8 g of sodium hydroxide were dissolved in 40 ml of methanol and the above dioxane solution was added to this solution. The mixture was refluxed for 6 hours, after which the solvent was distilled off. To the residue was added ethyl acetate and the mixture was washed with 1N-hydrochloric acid and saturated aqueous sodium chloride solution and the solvent was distilled off under reduced pressure. The residue was dissolved in 50% methanol and the solution was adjusted to pH 6.0 by gradual addition of methanolic sodium hydroxide solution. To this solution was added ethyl alcohol, and the resulting crystals were collected by filtration to provide 3.0 g of the sodium salt of the title compound. m.p. 194°–196° C. (decomp.)

Elemental analysis for $C_{36}H_{60}O_7NNa$ Calcd. (%): C, 67.37; H, 9.42; N, 2.18 Found (%): C, 67.14: H, 9.22; N. 1.85

Example 6

N-[3-(α-Tocopher-6-yloxy)-2-hydroxypropyl]glutamic acid

[$R_1$50 $R_2=CH_3$, $R_3=NHCH(COOH)CH_2CH_2COOH$]

Using 4.3 g of DL-α-tocopherol and 5 ml of epichlorohydrin, the reaction procedure described in Example 1 was repeated to prepare (2,3-epoxypropane)tocopherol, followed by addition of 20 ml of dioxane. On the other hand, 1.5 g of L-glutamic acid and 0.8 g of sodium hydroxide were dissolved in 40 ml of methanol and the above dioxane solution was added to this solution. The same reaction as that of Example 5 was then carried out to provide 0.3 g of the sodium salt of the title compound. m.p. 151°–153° C. (decomp.)

Elemental analysis for $C_{37}H_{62}O_7NNa \cdot 1/2H_2O$ Calcd. (%): C, 66.84; H, 9.55; N, 2.11 Found (%): C, 66.65; H, 9.54; N, 1.98

Formulation Example 1

Oral tablets

| Compound of Example 1 | 50 mg |
| Lactose | 80 mg |
| Starch | 17 mg |
| Magnesium stearate | 3 mg |

Using the above ingredients per tablet, tablets are manufactured by the routine procedures. Where necessary, the tablets may be sugar-coated.

Formulation Example 2

Ophthalmic solution

| Compound of Example 4 | 100 mg |
| Boric acid | 700 mg |
| Borax | 400 mg |

-continued

| | |
|---|---|
| Sodium chloride | 500 mg |
| Methyl p-hydroxybenzoate | 26 mg |
| Butyl p-hydroxybenzoate | 14 mg |
| Sterile purified water | to make 100 ml |

The above ingredients are mixed in the routine manner to provide an ophthalmic solution.

Formulation Example 3

Injection

| | |
|---|---|
| Compound of Example 4 | 100 mg |
| Sodium chloride | 900 mg |
| 1N-Hydrochloric acid | q.s. |
| Distilled water | To make 100 ml pH 7.5 |

The above components are admixed in the routine manner to provide an injection.

Formulation Example 4

Ointment

| | |
|---|---|
| Compound of Example 3 | 1000 mg |
| Hydrophilic ointment base | to make 100 g |

The above ingredients are admixed in the routine manner to provide an ointment.

The tocopherol derivative of this invention is a compound which is water-soluble and can be expected to be of use as a cerebral function-improving drug and an anticataract drug. Moreover, this compound is of value as an UV-absorber, a skin care ingredient, or a stabilizer for other cosmetic ingredients.

What is claimed is:

1. A tocopherol derivative of the following formula (I) or a pharmacologically acceptable salt thereof

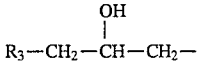
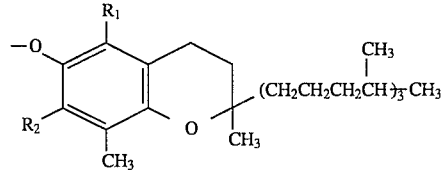

wherein $R_1$ and $R_2$ are the same or different and each represents hydrogen or methyl; $R_3$ represents a member selected from the group consisting of glycine, alanine, proline, cysteine, glutamic acid, aspartic acid, β-alanine, γ-aminobutyric acid, ε-aminocaproic acid, 2-aminoethanesulfonic acid, and glutathione.

2. The tocopherol derivative or pharmacologically acceptable salt thereof according to claim 1 wherein $R_3$ is cysteine.

3. The tocopherol derivative or pharmacologically acceptable salt thereof according to claim 1 wherein $R_3$ is 2-aminoethanesulfonic acid.

4. The tocopherol derivative or pharmacologically acceptable salt thereof according to claim 1 wherein $R_3$ is γ-aminobutyric acid.

5. The tocopherol derivative or pharmacologically acceptable salt thereof according to claim 1 wherein $R_3$ is glutathione.

6. The tocopherol derivative or pharmacologically acceptable salt thereof according to claim 1 wherein $R_3$ is aspartic acid.

7. The tocopherol derivative or pharmacologically acceptable salt thereof according to claim 1 wherein $R_3$ is glutamic acid.

* * * * *